United States Patent [19]
Labigne

[11] Patent Number: 5,811,237
[45] Date of Patent: *Sep. 22, 1998

[54] NUCLEOTIDE SEQUENCES CODING FOR A PROTEIN WITH UREASE ACTIVITY

[75] Inventor: Agnès Labigne, Beauséjour, France

[73] Assignees: Institut Pasteur; Institut Nationale de la Sante et de la Recherche Medicale, both of Paris, France

[*] Notice: The term of this patent shall not extend beyond the expiration date of Pat. No. 5,610,707.

[21] Appl. No.: 470,245

[22] Filed: Jun. 6, 1995

Related U.S. Application Data

[62] Division of Ser. No. 499,325, filed as PCT/FR89/00518 Oct. 6, 1989.

[30] Foreign Application Priority Data

Oct. 6, 1988 [FR] France .................................. 88 13135

[51] Int. Cl.⁶ .............................. C12P 19/34; C12Q 1/68; C07H 1/04; C12N 9/78
[52] U.S. Cl. ............................. 435/6; 435/91.2; 435/227; 536/23.1; 536/23.2; 536/24.32; 935/77; 935/78
[58] Field of Search ................................ 435/6, 91.2, 227; 536/23.2, 24.32; 935/77, 78

[56] References Cited

FOREIGN PATENT DOCUMENTS

WO96/33732 10/1996 WIPO.

OTHER PUBLICATIONS

Wetherall, B.L. et al, Med. Microbiol., 26: 257–263 (1988).
Clayton et al., Infect. Immun. 57(2):623–629 (Feb. 1989).
Clayton et al., Nuc. Acids Res. 18(2):362 (1990).
Collins et al., J.Bact. 170(3):1041–1045 (Mar. 1988).

*Primary Examiner*—Stephanie W. Zitomer
*Attorney, Agent, or Firm*—Finnegan, Henderson, Farabow, Garrett & Dunner, L.L.P.

[57] ABSTRACT

The invention relates to a sequence of nucleotides, characterized in that it comprises at least a part of a sequence coding for a protein with urease activity such as that expressed by *C. pylori*.

Another subject of the invention is the uses of this sequence, in particular for the in vitro diagnosis of diseases associated with the presence of *Campylobacter pylori* in the organism of an individual.

15 Claims, 1 Drawing Sheet

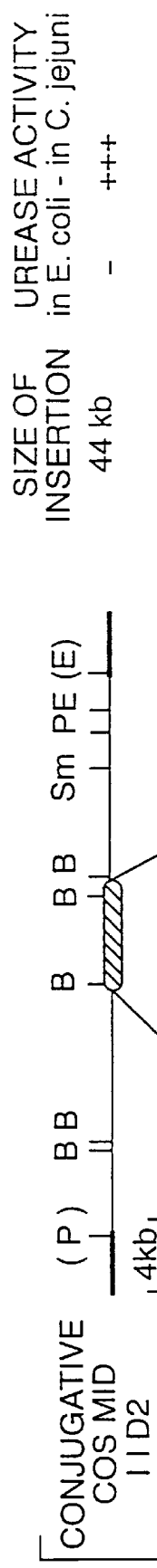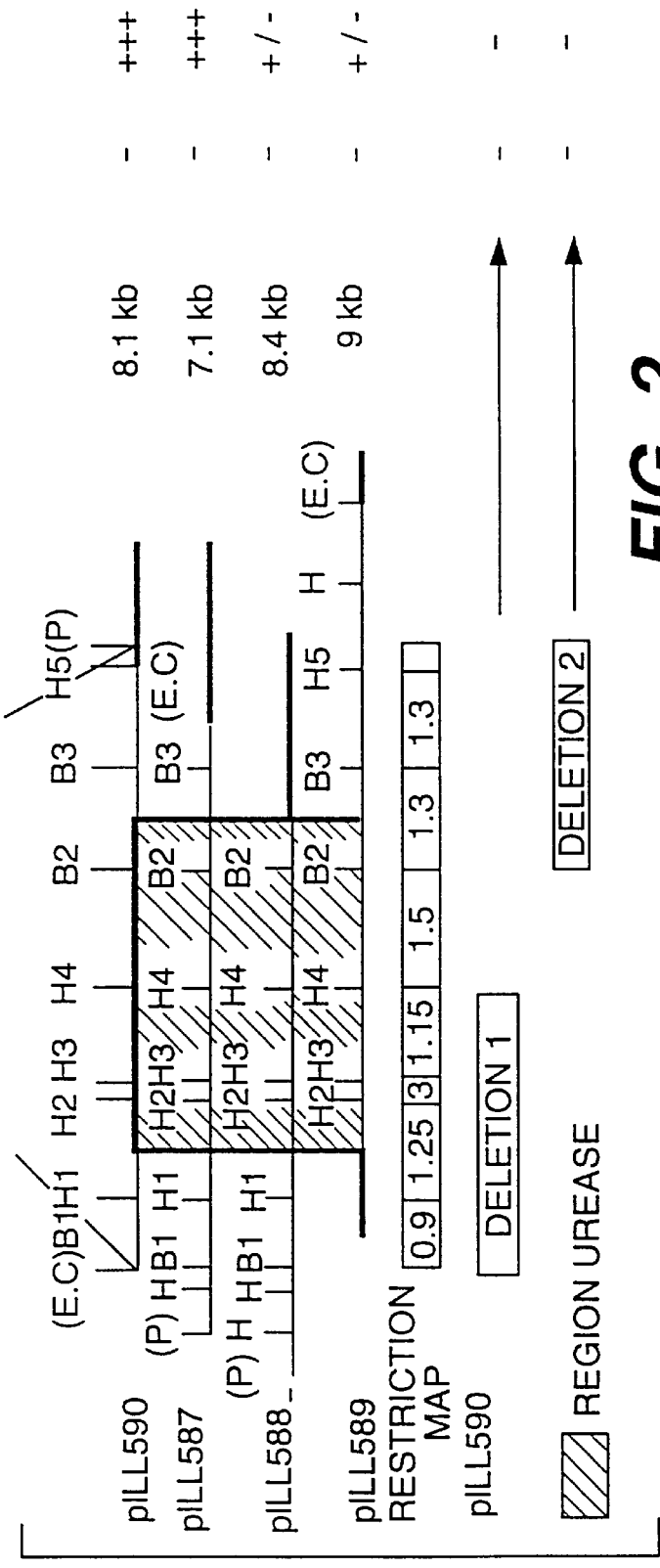

NUCLEOTIDE SEQUENCES CODING FOR A PROTEIN WITH UREASE ACTIVITY

This is a division of application Ser. No. 07/499,325, filed Jun. 5, 1990, filed as PCT/FR89/00518 Oct. 6, 1989.

The subject of the invention is nucleotide sequences coding for a urease such as that naturally expressed in *Campylobacter pylori* and its biological uses, in particular for the detection of *C. pylori* in man or in the environment.

BACKGROUND OF THE INVENTION

*C. pylori* is a Gram negative bacterium found at present exclusively at the surface of the mucous membranes of the antral part of the stomach in man, and more particularly around the lesions and craters of gastric and duodenal ulcers. 25% of the population are carriers of *C. pylori*: 8% have an ulcerous disease, 9% suffer from non-ulcerous dyspepsia and 8% are asymptomatic carriers.

All of the *C. pylori* isolated and described up to the present possess the three following properties:

The bacteria produce a urease endowed with high activity.

They adhere very tightly to epithelial cells of the gastric mucosa, this property being reflected in vitro in a very tight adhesion to Hela cells.

The *C. pylori* produce and release an enzyme possessing a proteolytic activity leading to the degradation of mucus and, hence, to a weakening of the barrier which naturally protects the gastric mucosa.

The detection of *C. pylori* in situ in man and in the environment and the study of its pathogenicity—it is considered as being responsible for active gastrites in man—is, however, confronted with difficulty with respect to the culture of this organism.

Its growth is very slow (6 to 7 days on blood agar medium) and it must be grown under microaerophilic conditions, the oxygen of the air being toxic.

The search for agents to detect this bacterium has led the investigators to identify the genes in *C. pylori* responsible for the production of urease.

The determination of the nucleotide sequence of an intragenic fragment has made available a tool which can be used as detection probe for the specific identification of the *C. pylori*.

SUMMARY OF THE INVENTION

Thus, the aim of the invention is to provide novel sequences of nucleotides capable of coding for proteins with urease activity such as that expressed in *C. pylori*.

Another aim of the invention is to provide fragments of this sequence which can be used as probes for the detection of *C. pylori*.

In addition, the invention aims to provide a protein with urease activity such as that expressed in *C. pylori* of high purity, and fragments of this protein.

BRIEF DESCRIPTION OF THE DRAWINGS

FIG. 1 depicts a restriction map of a PstI-EcoRI fragment of the recombinant cosmid IID2 carrying the information required for the expression of urease in *C. jejuni*.

FIG. 2 depicts a restriction map of a fragment of about 8 kb of pILL590.

DESCRIPTION OF THE PREFERRED EMBODIMENTS

The sequence of nucleotides according to the invention is characterized in that it comprises at least a part of a sequence coding for a protein with urease activity such as that expressed in *C. pylori*.

More particularly, the subject of the invention is a sequence of nucleotides capable of hybridizing with genes coding for a protein with urease activity such as that expressed in *C. pylori*, under the following conditions: 68° C., 6×SSC (1×SSC is constituted by 0.15M of NaCl and 0.015M of sodium citrate, pH7) in Denhardt medium (1% Ficoll, 1% polyvinylpyrrolidone, 1% of bovine serum albumin).

In accordance with another feature of the invention, the sequence of nucleotides is characterized in that it carries the information required for the production of a protein with urease activity or of its fragments, capable of forming an immunological complex with antibodies directed against a protein with urease activity such as that expressed in *C. pylori* or against fragments of the latter, respectively.

The sequence according to the invention is also characterized in that it comprises at least a part of a fragment of about 8 kb corresponding to the restriction fragment EcoRI (ClaI, BamHI)-PstI (HindIII).

The enzymatic restriction map of this fragment is shown in FIG. 2.

A more especially preferred sequence comprises at least a part of a fragment of about 4.2 kb (±5%) delimited by the terminal nucleotides situated at a distance of about 0.55 kb upstream from the H2 site shown in FIG. 2, and about 0.7 kb downstream from the B2 site shown in FIG. 2, respectively.

The sequences constituted by this fragment carry the information necessary for the expression of a protein with urease activity such as that expressed naturally in *C. pylori*.

The expression of these sequences can be induced in any other microorganism capable of taking advantage of the information carried by these sequences, in particular in a strain of Campylobacter naturally deficient in genes coding for the production of a protein with urease activity (or thus a strain of Campylobacter urease$^-$).

In accordance with another feature, the invention relates to a recombinant sequence comprising one of the sequences defined above, if necessary combined with a promoter capable of controlling the transcription of the sequence and a DNA sequence coding for the termination signals of transcription.

The nucleotide sequences of the invention are characterized in that they are capable of hybridizing with a probe formed from the sequence possessing:

the following nucleotide sequence (I):

```
AAGCTTTTAGGGGTGTTAGGGGTTTATCAAAAATCTAAAAACGCCCTTTCTTCTCAAGCA
ATTGTCGCTACAAACATGAGCAATTTAGCCCTTAAAGAATACTTAAAATCCCAAGATTTA
GAATTGAAGCATTGCGCGATTGGGGATAAGTTTGTGAGCGAATGCATGCGATTGAACAAA
GCCAATTTTGGAGGCGAGCAAAGCGGGCATATCATTTTTAGCGATTACGCTAAAACCGGC
GATGGCTTGGTGTGCGCTTTGCAAGTGAGCGCGTTAGTGTTAGAAAGTAAGCTT
``` or the following nucleotide sequence (II):

```
AACGCATGATTGATTGCAGAAGGAGTGGTGCCCCAGTCTTCGTGAATTTTAAAGCCAATC
GCACCGGCTTCAATTTGATCGGCTAAGCTCGCATCGTTAGAAGCGTTACCTTTAGCCAAG
AAACCTAAATTCATAGAATATTCTTCAGCCGCTCTGAGCATCCATTTTAAATTTCTTCTG
CCTGGAGTGATAGTAGTCGCATTAGTGCCATCAGCAGGACCGGTTCCACCACCAATCATG
GTTGTTACACCGCTTCGAAAAGCTGTAGGGATTTGTTGGGGTGAAATGAAGTGGATGTGT
GTGTCAATACCACCAGCCGTTACGATCAAACCTTCACCGGCTAAGGCTTCAGTAGCAGGA
CCTACGCTAAGATTGTTTTTAACGCCATCTTGCATGTCTTTGTTACCGCCTTTACCAATG
CCAGCGATTTTGCCATCTTTAATACCAATATCCGCTTTATAAATACCGGTGTAATCCACG
ATTAAAGCGTTAGTGATAATTAAATCCAACTCTTCTTTGCTAGGGTTGTTAGATTGGCTG
ATGCCTTCTCTTAGGGGTTTTACCGCCACCGAATTTAAGCTCTTCGCCATAAATGGTGTA
GTCATGTTCTACTTCAGCGATCAAGTCTGATCGCCCAATCTCACTTTATCGCCTGTAGTA
GGACCATACATAGAAACATATTCTTTTCTGCTAATCTTTTTCATTTCTTACTCCTTAATT
GTTTTTACATAGTTGTCATCGCTTTAGG
``` or the following nucleotide sequence (IIbis):

```
CCTAAAAGCGATGACAACTATGTAAAAACAATTAAGGAGTAAGAAATGAAAAAGATTAGC
AGAAAAGAATATGTTTCTATGTATGGTCCTACTACAGGCGATAAAGTGAGATTGGGCGAT
CAGACTTGATCGCTGAAGTAGAACATGACTACACCATTTATGGCGAAGAGCTTAAATTCG
GTGGCGGTAAAACCCCTAAGAGAAGGCATGAGCCAATCTAACAACCCTAGCAAAGAAGAG
TTGGATTTAATTATCACTAACGCTTTAATCGTGGATTACACCGGTATTTATAAAGCGGAT
ATTGGTATTAAAGATGGCAAAATCGCTGGCATTGGTAAAGGCGGTAACAAAGACATGCAA
GATGGCGTTAAAAACAATCTTAGCGTAGGTCCTGCTACTGAAGCCTTAGCCGGTGAAGGT
TTGATCGTAACGGCTGGTGGTATTGACACACACATCCACTTCATTTCACCCCAACAAATC
CCTACAGCTTTTCGAAGCGGTGTAACAACCATGATTGGTGGTGGAACCGGTCCTGCTGAT
GGCACTAATGCGACTACTATCACTCCAGGCAGAAGAAATTTAAAATGGATGCTCAGAGCG
GCTGAAGAATATTCTATGAATTTAGGTTTCTTGGCTAAAGGTAACGCTTCTAACGATGCG
AGCTTAGCCGATCAAATTGAAGCCGGTGCGATTGGCTTTAAAATTCACGAAGACTGGGGC
ACCACTCCTTCTGCAATCAATCATGCGTT
``` or nucleotide sequences complementary to the above-mentioned sequences (I), (II) and (IIbis), respectively.

Nucleotide sequences according to the invention are characterized in that they comprise the nucleotide sequences defined above or are constituted by at least a part of these sequences.

It will be obvious that the bases of the nucleotide sequences considered may be in a different order from that found in the genes and/or that these bases may be, if required, substituted once a probe, constructed from such sequences, gives a characteristic response and not an equivocal one with respect to its capacity to recognize the presence of genes coding for the protein with urease activity in C. pylori.

Any sequence of nucleotides which can hybridize with the above-mentioned nucleotide sequences such as that obtained by reverse enzymatic transcription of the corresponding RNA or also produced by chemical synthesis, are also included in the scope of the invention.

The invention also relates to a nucleotide sequence corresponding, according to the universal genetic code, to at least a part of the following amino acid sequence (III):

Another subject of the invention is a sequence of nucleotides corresponding, according to the universal genetic code, to at least a part of the following amino acid sequence (IV):

NMTTPFMAKSINSVAVKPLREGMSQSNNPSKEELDLIITNALIVDYTGIYKADIGIKDGK
LAGIGKGGNKDMQDGVKNNLSVGPATEALAGEGLIVTAGGIDTHIHFISPQQIPTAFRSG
VTTMIGGGTGPADGINATTITPGRRNLKWMLRAAEEYSMNLGFLAKGNASNDASLADQIE
AGAIGFKIHEDWGTTPSAINHA

The invention also relates to recombinant expression and cloning vectors, capable of transforming a suitable cell host and containing at least a part of a nucleotide sequence such as that defined above under the control of regulatory elements making possible its expression.

Preferred recombinant vectors contain at least a part of the sequence of about 4.2 kb mentioned above.

The transformed strains of microorganisms are also included in the scope of the invention. These strains contain one of the nucleotide sequences defined above or also a recombinant vector such as that previously defined.

The strain E. coli S17-1 deposited on Jul. 28, 1988 under the No. I795 with the National Collection of Cultures of Microorganisms (N.C.C.M) 28 rue du Docteur Roux, 75724 Paris Cedex 15, France carries the plasmid pILL590 of about KLLGVLGVYQKSKNALSSQAIVATNMSNLALKEYLKSQDLELKHCAIGDKFVSECMRLNK
ANFGGEQSGHIIFSDYAKTGDGLVCALQVSALVLESKL 16.3 kb which comprises the restriction fragment EcoRI (ClaI, BamHI)-PstI (HindIII) of about 8 kb mentioned above.

In addition, the invention relates to a protein possessing urease activity of the type expressed naturally in C. pylori as well as peptide fragments of this protein.

The protein of the invention and its fragments correspond, according to the universal genetic code, to the nucleotide sequences defined above, in particular to at least a part of the sequence of about 4.2 kb.

The protein of the invention is also characterized in that it is a protein such as that obtained by transformation of host cells by means of a recombinant vector such as that defined above, the placing in culture of the transformed host cells in a suitable medium and the recovery of the protein from these cells or, directly, from the culture medium. The production of urease or fragments of the latter by this procedure is also included in the invention.

The protein of the invention and its fragments, which may also be obtained by chemical synthesis, advantageously possess a high degree of purity and can be used to form polyclonal antibodies according to standard techniques.

Such polyclonal antibodies as well as the monoclonal antibodies capable of recognizing specifically the above protein and its fragments are also included in the invention.

The nucleotide sequences defined above are obtained according to standard techniques of genetic engineering by cloning and identification of the genes responsible for the synthesis of a protein with urease activity in C. pylori.

The invention also relates to the biological uses of the nucleotide sequences, of the corresponding proteins and of the monoclonal or polyclonal antibodies.

These uses include the construction of probes for the detection of C. pylori starting from intragenic fragments. This construction comprises, in particular, the denaturation of the double-stranded sequences in order to produce a single-stranded sequence which can be used as a probe.

The assays carried out with such fragments to detect the possible presence of complementary sequences in various Campylobacter and in microorganisms belonging to different genera have demonstrated the high specificity of these fragments.

Thus, the invention relates to detection probes characterized in that they comprise at least a part of one of the nucleotide sequences defined above.

Every probe differing from the preceding one at the level of its nucleotide sequence only by substitutions or nucleotide changes not leading to a modification of its hybridization properties with the genome of C. pylori is included in the scope of the invention.

The DNA fragment used as probe contains the number of nucleotides sufficient to produce the required specificity and the formation of a stable hybrid.

It is possible to use fragments attaining several kb, although results of high specificity are also obtained with shorter fragments of about 25 to 40 nucleotides.

Probes suitable for this type of detection are advantageously labelled with a radioactive element or any other group enabling it to be recognized in a state of hybridization with the preparation containing the DNA under study.

In accordance with standard techniques, these probes are placed in contact with a biological sample containing bacteria, or directly with these bacteria or their nucleic acids under conditions which permit the possible hybridization of the nucleotide sequence of the probe with a complementary sequence, possibly contained in the product tested.

For example, use may be made of the spot hybridization method. After denaturation of the DNA previously obtained from bacteria derived from antral biopsies, this method consists in the deposition of aliquots of this DNA on nitrocellulose membranes, the hybridization of each membrane under the usual conditions with the probe and the detection of the hybrid formed in the standard manner.

Use may also be made of the replica hybridization method according to the technique of Southern. This method comprises the electrophoretic separation in agarose gel of the DNA fragments obtained after treatment of the DNAs by restriction enzymes, transfer after alkaline denaturation to suitable membranes and their hybridization with the probe under the usual conditions. It is not always necessary to first induce the expression of the DNA. It is sufficient for the DNA to be made accessible to the probe.

Detection for the specific identification of the C. pylori can also be carried out by DNA amplification techniques (PCR). These techniques are described in particular in the patents U.S. Pat. Nos. 4,683,202 and 4,683,195 in the name of the Cetus Corporation.

For the implementation of these techniques, two primers from 10 to 40 nucleotides long are used, advantageously about twenty nucleotides long, these primers being contained in one of the nucleotide sequences defined above, or being capable of hybridizing with part of one of the nucleotide sequences defined above, or with their complementary sequences. Advantageously, these primers are separated from each other by about 200 to 250 nucleotides when they hybridize (or bind) with strands of the DNA to be amplified. One of the sequences is capable of binding to a nucleotide sequence of one of the strands of the DNA fragment to be amplified, this sequence being situated at one end of this fragment (for example, the 5' end); the other sequence is capable of binding to a nucleotide sequence of the second strand of the DNA fragment to be amplified, this latter sequence being situated at the opposite end of this fragment to that mentioned above (in the example suggested, this latter end being designated by the 3'end).

Preferred primers are included in the nucleotide sequence of the H2-H3 restriction fragment of FIG. 2, and are separated from each other by about 200 to 250 nucleotides.

In particular, they are fragments at each end of this restriction sequence HindIII-HindIII.

An in vitro screening procedure for the possible presence of C. pylori in a biological sample comprises the following steps:

possible prior amplification of the amount of nucleotide sequences likely to be contained in the sample by placing in contact of this sample with primers such as those described above, capable of binding, respectively, to the 5' end of a strand of the said sequence of nucleotides, on the one hand, and to the 3' end of the other strand of the said nucleotide sequence, on the other, this placing in contact being followed by a genic amplification step in the presence of a DNA polymerase and the four nucleosides triphosphate dATP, dCTP, dGTP, dTTP, these primers hybridization and genic amplification operations being repeated several times, the placing in contact of the biological sample in question with a nucleotide probe according to the invention under conditions leading to the production of a hybridization complex formed between the probe and the nucleotide sequence, the detection of the hybridization complex.

The invention thus provides tools making possible the rapid detection of C. pylori in situ, and in the environment with high specificity without the need to grow cultures.

Such tools of detection are particularly useful for the study of the natural reservoir of these bacteria, the methods of their transmission, spread and contamination. Furthermore, in the in vitro diagnosis practiced in biopsies, the utilization of such probes makes possible a considerable saving of time compared with the techniques presently used which, in addition, require a technology which can only be carried out in specialized departments, namely bacteriological techniques or those making use of the electron microscopy.

Reproducible results have been obtained by using as intragenic probe the fragment of about 8 kb defined above.

On account of their specificity for *C. pylori*, these probes also constitute a tool of great value.

In order to study the pathogenicity of *C. pylori* so as to prevent infection, it is thus possible to study the role played by *C. pylori* in the development of ulcerous diseases and to identify the genetic determinants which appear to be implicated in the pathogenicity of this organism with the view to creating in vitro isogenic mutants of *C. pylori*, i.e. bacteria genetically modified in each of the determinants which appear to play a role in the pathogenesis of the infection, mutants which it will be possible to test in animal models.

The invention also relates to the detection of the polymorphism of the genes coding for the urease in *C. pylori* with the aid of the nucleotide probes defined above and suitable restriction enzymes. The conditions under which this detection is carried out are described more particularly in the article of Gusella J. F. in J. of Clin. Investigations (1986), 77, 1723–1726.

The invention also relates to immunological applications of the coded protein, more especially to the preparation of a specific antiserum as well as polyclonal and monoclonal antibodies. The polyclonal antibodies are formed according to the standard techniques by injection of the protein into animals, recovery of the antisera, then of the antibodies from the antisera by means, for example, of affinity chromatography.

The monoclonal antibodies are produced in the usual manner by fusing myeloma cells with the spleen cells of animals immunized beforehand with the proteins of the invention.

In addition, the invention relates to an in vitro screening procedure for the possible presence of *C. pylori* in a biological sample likely to contain it. This procedure is characterized in that it comprises:

the placing in contact of the sample with an antibody according to the invention under conditions leading to the production of an immunological complex formed between all or part of the protein with urease activity produced by *C. pylori* and this antibody, and the detection of the immunological complex.

For the implementation of the in vitro screening methods, considered above and based on the utilization of nucleotide probes, recourse is advantageously had to kits containing:

if necessary, at least one couple of primers according to the invention, a defined amount of a nucleotide probe according to the invention, advantageously, a medium suitable for the formation of a hybridization reaction between the sequence to be detected and the probe, advantageously, reagents capable of detecting the hybridization complexes formed between the nucleotide sequence and the probe subsequent to the hybridization reaction.

For the implementation of the in vitro screening methods defined above, based on the utilization of antibodies, recourse is advantageously had to kits comprising:

a defined amount of an antibody according to the invention, advantageously, a medium suitable for the formation of an immunological reaction between at least a part of the protein with urease activity produced by a strain of *C. pylori* and the antibody, advantageously, reagents capable of detecting the immunological complexes formed between at least a part of the protein with urease activity and the antibody subsequent to the immunological reaction.

A careful study of the 4.2 kb fragment defined above has made possible to locate the structural genes coding for the major polypeptide subunits of the urease of *C. pylori*.

This study has been carried out by constructing mutants in the recombinant plasmids introduced in *E. coli* and *C. jejuni* not capable of synthesizing urease (Baskerville, A., Newell D. (1988), Gut. 29, 465–472). The in vitro transcription-translation system of *E. coli*, as also an expression system in minicells, have been used in order to identify and localize, in the 4.2 kb fragment of *C. pylori*, all the genes coding for the urease subunits: two major proteins of 2.6 kDa and 61 kDa have been identified. In a parallel direction, after various deletions in the 4.2 kb fragment, a transfer system to *C. pylori* (of the type of the one described in the detailed description which follows) has been used to identify the areas essential to the expression of the urease activity and to correlate the deletion of an area with the removal of a polypeptide and the loss of the urease activity. Thus, it has been determined that genes coding for the two polypeptides required for the expression of the urease activity are situated in the central area of 3.35 kb, downstream from the H3 site of the FIG. 2, and overlapping B2. The transcription of genes coding for polypeptides of 61 kDa or 26 kDa is carried out in the EcoRI-PstI direction. The 3.35 kb fragment is essential, but not sufficient, to the expression of the urease activity in *C. jejuni*. An adjacent area of 0.85 kb, situated upstream, and apparently not associated with he expression of polypeptides in *E. coli*, is essential to the expression of the urease activity in *C. jejuni*.

The analysis of the deletion mutants by in vitro transcription-translation has made possible to observe that the two polypeptides of 26 kDa and 61 kDa are coded by two adjacent DNA fragments.

The present invention relates to all or part of the following nucleotide sequence (V):

```
ATGAAACTCACCCCAAAAGAGTTAGATAAGTTGATGCTCCACTACGCTGGAGAATTGGCT
AAAAAAACGCAAAGAAAAAGGCATTAAGCTTAACTATGTAGAAGCAGTAGCTTTGATTAGT
GCCCATATTATGGAAGAAGCGAGAGCTGGTAAAAAGACTGCGGCTGAATTGATGCAAGAA
GGGCGCACTCTTTTAAAACCAGATGATGTGATGGATGGCAAGCATGATCCATGAA
GTGGGTATTGAAGCGATGTTTCCTGATGGGACTAAACTCGTAACCGTGCATACCCCTATT
GAGGCCAATGGTAAATTAGTTCCTGGTGAGTTGTTCTTAAAAAATGAAGACATCACTATC
AACGAAGGCAAAAAAGCCGTTAGCGTGAAAGTTAAAAATGTTGGCGACAGACCGGTTCAA
ATCGGCTCACACTTCCATTTCTTTGAAGTGAATAGATGCCTAGACTTTGACAGAGAAAAA
ACTTTCGGTAAACGCTTAGACATTGCGAGCGGGACAGCGGTAAGATTTGAGCCTGGCGAA
GAAAAATCCGTAGAATTGATTGACATTGGCGGTAACAGAAGAATCTTTGGATTTAACGCA
TTGGTTGATAGACAAGCAGACAACGAAAGCAAAAAAATTGCTTTACACAGAGCTAAAGAG
CGTGGTTTTCATGGCGCTAAAAGCGATGACAACTATGTAAAAACAATTAAGGAGTAA
                                                                                717
```

The invention relates more particularly to any nucleotide sequence corresponding, according to the universal genetic code, to at least one part of the following amino-acid sequence (VI) of 26 kDa (coded by the nucleotide sequence (V)):

```
1
MKLTPKELDKLMLHYAGELAKKRKEKGIKLNYVEAVALLSAHIMEEARAGKKTAAELMQE
GRTLLKPDDVMDGVASMIHEVGIEAMFPDGTKLVTVHTPIEANGKLVPGELFLKNEDITI
NEGKKAVSVKVKNVGDRPVQIGSHFHFFEVNRCLDFDREKTFGKRLDIASGTAVRFEPGE
EKSVELIDIGGNRRIFGFNALVDRQADNESKKIALHRAKERGFHGAKSDDNYVKTIKE
    239 aminoacids                                                      239
```

Molecular weight: 26522 daltons.

The invention also relates to all or part of the following nucleotide sequence (VII):

The invention relates more particularly to any nucleotide sequence corresponding, according to the universal genetic code, to at least one part of the following amino acid sequence (VIII) of 61 kDa (coded by the nucleotide sequence (VII)):

The invention also relates to all or part of the nucleotide sequence (IX) constituted successively by the sequence (V) and the sequence (VII).

The invention also relates to all nucleotide sequences corresponding, according to the universal genetic code, to at least one part of the aminoacids sequence (X) of 87 kDa constituted successively of the sequence (VI) and the sequence (VIII).

The invention also relates to detection probes of the possible presence of C. pylori in a biological sample, characterized in that they comprise at least one part of a nucleotide sequence defined above.

```
1
MKKISRKEYVSMYGPTTGDKVRLGDTDLIAEVEHDYTIYGEELKFGGGKTLREGM

SQSNNPSKEELDLIITNALIVDYTGIYKADIGIKDGKIAGIGKGGNKDMQDGVKNN

LSVGPATEALAGEGLIVTAGGIDTHIHFISPQQIPTAFASGVTTMIGGGTGPAD

GTNATTITPGRRNLKWMLRAAEEYSMNLGFLAKGNASNDASLADQIEAGAIGF

KIHEDWGTTPSAINHALDVADKYDVQVAIHTDTLNEAGCVEDTMAAIAGRTMH

TFHTEGAGGGHAPDIIKVAGEHNILPASTNPTIPFTVNTEAEHMDMLMVCHHLD

KSIKEDVQFADSRIRPQTIAAEDTLHDMGIFSITSSDSQAMGRVGEVITRTWQT

ADKNKKEFGRLKEEKGDNDNFRIKRYLSKYTINPAIAHGISEYVGSVEVGKVADL

VLWSPAFFGVKPNMIIKGGFIALSQMGDANASIPTPQPVYYREMFAHHGKAKYD

ANITFVSQAAYDKGIKEELGLERQVLPVKNCRNITKKDMQFNDTTAHIEVNPETY

HVFVDGKEVTSKPANKVSLAQLFSIF_
569 amino acids                 569
```

Molecular weight: 61729 daltons.

The comparison between the amino acid sequence (VIII) with the Jack bean urease sequence described in Eur. J. Biochem., 175, 151–165 (1988), shows in an unexpected manner a high level of homology of amino acids. This conservation of structure has led the investigators to deduce that the active site of the urease subunit of 61 kDa, which is comprised, in totality or in part, in the polypeptide sequence delimited by the amino acids situated at positions 206 and 338 of the sequence VIII described above.

It will be obvious that the bases of the nucleotide sequences can be in a different order than the one found in the genes and/or that these bases can be, if required, substituted, one a probe, constructed from such sequences, gives a characteristic response with respect to its capacity to recognize the presence of genes coding for the protein with urease activity in C. pylori.

Any sequence of nucleotides which can hybridize with the above mentioned nucleotide sequences such as that obtained by reverse enzymatic transcription of the corresponding RNA or also produced by chemical synthesis are also included in the scope of the invention.

Every probe which differs from the preceding one; at the level of its nucleotide sequence, only by substitution or nucleotides changes not leading to a modification of its hybridization properties with the genome of C. pylori, is included in the scope of the invention.

The probes above mentioned can be used in the in vitro diagnosis processes described above of the possible presence of C. pylori in a biological sample.

The invention also relates to nucleotide primers from about 10 to about 40 nucleotides, these primers being contained in one of the nucleotide sequence (V) or (VII) defined above (or in one of the sequence derived from these sequences (V) and (VII)), or being capable of hybridizing with one part of one of the nucleotide sequences above-mentioned or with their complementary sequences (more particularly in the hybridization conditions defined above).

The invention also relates to the use of these primers in the in vitro diagnosis methods defined above, for the prior amplification of the quantity of nucleotides of C. pylori likely to be contained in the biological sample according to the process described above.

The invention also relates to recombinant expression and cloning vectors, capable of transforming a suitable host cell comprising all or part of a nucleotide sequence identical to or derived from the nucleotide sequences (V), (VII), and (IX) above-mentioned.

The invention also relates to a process for the production of proteins corresponding to all or part of the sequences (VI), (VIII), and (X) above-mentioned, this process comprising the transformation of suitable host cells (more particularly those described above) with the aid of the vectors above-mentioned, and the recovery of the proteins thus produced followed, if required, by a purification step of these proteins.

The proteins production process defined above comprises, if required, a prior amplification step of the gene coding for the protein which production is wanted, this step being carried out with the aid of couple of primers of the invention according to the process described above.

The invention also relates to polypeptides (or proteins) coded by the nucleotide sequences described above. In particular, the invention relates to the amino acid sequence (X) of 87 kDa, the sequence (VI) of 26 kDa, and the sequence (VIII) of 61 kDa described above, and to their fragments.

The invention also relates to polyclonal or monoclonal antibodies obtained from all or part of the polypeptides described above and capable of forming an immunological complex with them.

The invention more particularly relates to antibodies, in particular monoclonal, obtained with the aid of a peptide sequence of at least 10 to 15 amino acids of the sequence (VI), or the sequence (VIII).

Preferred monoclonal antibodies of the invention are directed against all or part of the sequence delimited by the amino acids situated at positions 206 and 338 of the sequence (VIII), and more particularly, those obtained with the aid of a peptide sequence of at least about 10 to 15 amino acids issued from the sequence delimited by the amino acids situated at positions 206 and 338 of the sequence (VIII).

The invention also relates to the use of the above-mentioned antibodies for the implementation of in vitro diagnosis methods, and in kits for in vitro diagnosis of the infection of a person by C. pylori such as those described above.

The invention also relates to immunogenic compositions comprising all or part of the polypeptides described above, and more particularly, all or part of the polypeptide sequence delimited by the amino acids situated at positions 206 and 338 of the sequence (VIII), in association with a pharmaceutically acceptable carrier.

Such immunogenic compositions are usable as vaccine compositions for the prevention of the infection of a person by C. pylori.

The invention also relates to pharmaceutical compositions comprising one (or several) antibody such as those described above, and more particularly antibodies likely to form an immunological complex with all or part of the peptide sequence delimited by the amino situated at positions 206 and 338 of the sequence (VIII), in association with a pharmaceutically acceptable carrier.

Such pharmaceutical compositions according to the invention are usable for the treatment of pathologies linked to the infection of a person by C. pylori, in particular gastritis, and gastric and duodenal ulcers.

Other advantages and characteristics of the invention are reported in the description which follows relating to the cloning of the genes responsible for the production of the protein with urease activity in C. pylori, the sequencing of the region associated with the expression of the protein with urease activity and the specificity of nucleotide probes for the detection of C. pylori.

1) Establishment of a genomic bank in a shuttle cosmid vector; cloning of the genes implicated in the production of the urease in C. pylori.

The chromosomal DNA of the strain C. pylori (85P) is prepared so as to generate fragments of DNA of high molecular weight; about 300 ug of this chromosomal DNA are subjected to controlled partial digestion by means of the restriction endonuclease Sau3A and placed on a sucrose gradient so as to isolate selectively fragments of digestion included between 35 and 45 kilobases. 1.5 ug of these fragments are ligated in vitro to the shuttle vector-cosmid pILL575 linearised by the endonuclease BamHI and dephosphorylated. pILL575 was constructed from the shuttle cosmid pILL550 described by Labigne-Roussel et al. in J. Bacteriol. 169:5320–5323, 1987, in which the "cos" site of the lambda phage was inserted (Fragment Bgl II of 1.7 kb of pERG153 inserted at the Pvu II site of pILL550); like it, it can thus be mobilized by conjugation, codes for resistance to kanamycin which is expressed in both E. coli and Campylobacter (Km$^r$) and is replicated in both E. coli and in C. jejuni owing to the fact of the presence of two origins of replication, one functional in E. coli exclusively and the other only in Campylobacter. The products of this ligation are packaged in vitro in lambda particles, then introduced by transfection into a strain of E. coli carrying a plasmid IncP capable of trans complementation of the transfer functions of the recombinant cosmids. The colonies of E. coli, infected and resistant to kanamycin, are immediately stored individually at −80° C.; a cosmid genome bank representative of the entire genome of Campylobacter pylori is established in E. coli by preserving about 500 independent clones.

Each of the recombinant cosmids is then transferred by conjugation from E. coli to a receptor strain of Campylobacter jejuni C31, naturally urease.

A check is made for each of these kanamycin-resistant transconjugates as to whether urease is synthesized by Campylobacter jejuni.

Of 106 cosmids analysed, one is isolated carrying the genetic information conferring on Campylobacter jejuni C31 the capacity to produce a urease. The recombinant cosmid (IID2) has a size of 54 kilobases. The relative positions of the sites of cleavage by the restriction endonucleases PstI, BamHI, SmaI and EcoRI in this sequence are shown in FIG. 1.

2) Identification of the gene(s) required for the production of urease in *Campylobacter pylori*.

The subcloning of the urease genes is carried out by performing on the DNA of the cosmid IID2 prepared from *E. coli* partial digestions by means of the endonuclease Sau3A so as to generate fragments of partial digestion varying from 8 to 15 kilobases. The smallest hybrid plasaid cloned in *E. coli* conferring the capacity to produce a urease after transfer by conjugation to the *Campylobacter* receptor strain is isolated.

4 Plasmids out of the 37 tested carry the information necessary for the expression of the urease in *Campylobacter jejuni*: pILL587, pILL588, pILL589 and pILL590 (see FIG. 2). Plasmids pILL 587 and pILL 588 were deposited on Feb. 17, 1997 with the National Collection of Cultures of Microorganisms in Paris and assigned reference numbers I-1847 and I-1848, respectively.

On comparison of the restriction maps of these four hybrids, the presence of a sequence of nucleotides of 4.2 kilobases common to the four hybrids is observed, suggesting that that is the region required for the expression of the urease. A certain number of deletions were made which confirm these conclusions (see FIG. 2).

The EcoRI-PstI fragment of pILL590 was used as probe in hybridizations with the total DNA of *C. pylori* 85P with a view to ascertaining that the different restriction fragments generated by BamHI and HindIII from pILL590 were present in 85P. The results obtained show that the sequence of 8 kb present in pILL590 has not undergone rearrangements during the different cloning steps.

3) Sequence of nucleotides of the region associated with the expression of the urease.

The sequence of the HindIII fragment included between the H2 and H3 sites corresponds to the 294 nucleotides of the sequence (I).

The sequence of 610 nucleotides at the end of sequence (II) is contained within the fragment defined by the H4 and B2 sites (FIG. 2).

4) Specificity of the nucleotide probes for the detection of *Campylobacter pylori*.

The EcoRI-PstI fragment of 8 kb derived from pILL590 was used as radioactive probe in hybridization experiments.

32 Campylobacter pylori were tested in hybridization on colonies and gave a positive signal; of 35 Campylobacter strains), *Proteus vulgaris* (2 strains), *Providencia stuartii* (3 strains), *Pseudomonas picketti* (3 strains), *Yersinia enterocolitica* (3 strains), 5 strains of Acinetobacter urease$^+$, 2 strains of *Escherichia coli* urease$^+$ and 3 strains of *Citrobacter freundii* urease$^+$.

The absence of false positives with the 8 kb fragment guarantees the specificity of the nucleotide probes suggested.

A process for the preparation of antibodies comprises:

the immunization of an animal with a polypeptide defined above, and, the recovery of antibodies formed according to standard techniques.

An appropriate method for preparation of nucleic acids (comprising a maximum of 200 nucleotides—or bp, when it concerns bicatenary nucleic acids) of the invention, by chemical way, comprises the following steps:

the synthesis of DNA by using the automatized method of the beta-cyanethyl phosphoramidite described in Biorganic Chemistry; 4, 274–325 (1986), the cloning of the DNA such obtained in a plasmidic vector and the recovery of the DNA by hybridization with an appropriate probe.

A method for preparation, by chemical way, of nucleic acids of length higher than 200 nucleotides—or bp (when it concerns bicatenary nucleic acids) comprises the following steps:

the assembly of oligonucleotides chemically synthesized, provided at their ends with different restriction sites, which sequences are consistent with the amino acid sequence of the natural polypeptide according to the principle described in Proc. Nat. Acad. Sci., USA 80, 7461–7465 (1983), the cloning of the DNA such obtained in a plasmidic vector and the recovery of the DNA by hybridization with an appropriate probe.

I claim:

1. A purified nucleotide sequence comprising at least a part of the sequence coding for the urease protein expressed by *Campylobacter pylori*, wherein said part of a sequence is selected from the group consisting of sequence I, II, IIbis, V and VII.

2. A purified nucleotide sequence that specifically hybridizes with a nucleic acid probe having the following nucleotide sequence (I):

```
AAGCTTTTAGGGGTGTTAGGGGTTTATCAAAAATCTAAAAACGCCCTTTCTTCTCAAGCA
ATTGTCGCTACAAACATGAGCAATTTAGCCCTTAAAGAATACTTAAAATCCCAAGATTTA
GAATTGAAGCATTGCGCGATTGGGGATAAGTTTGTGAGCGAATGCATGCGATTGAACAAA
GCCAATTTTGGAGGCGAGCAAAGCGGGCATATCATTTTTAGCGATTACGCTAAAACCGGC
GATGGCTTGGTGTGCGCTTTGCAAGTGAGCGCGTTAGTGTTAGAAAGTAAGCTT;
```

Jejuni, fetus and *coli* studied none gave a positive signal under standard stringent conditions of hybridization (50% of formamide, 37°, 3×SSC).

Under the same conditions, the *C. pylori* probe of 8 kilobases did not give a positive signal with the list of the following microorganisms which are all natural producers of urease.

*Klebsiella oxytoca* (3 strains), *Klebsiella pneumoniae* (3 strains), *Proteus mirabilis* (3 strains), *Proteus morganii* (3 or the following nucleotide sequence (IIbis):

CCTAAAAGCGATGACAACTATGTAAAAACAATTAAGGAGTAAGAAATGAAAAAGATTAGC
AGAAAAGAATATGTTTCTATGTATGGTCCTACTACAGGCGATAAAGTGAGATTGGGCGAT
CAGACTTGATCGCTGAAGTAGAACATGACTACACCATTTATGGCGAAGAGCTTAAATTCG
GTGGCGGTAAAACCCCTAAGAGAAGGCATGAGCCAATCTAACAACCCTAGCAAAGAAGAG
TTGGATTTAATTATCACTAACGCTTTAATCGTGGATTACACCGGTATTTATAAAGCGGAT
ATTGGTATTAAAGATGGCAAAATCGCTGGCATTGGTAAAGGCGGTAACAAAGACATGCAA
GATGGCGTTAAAAACAATCTTAGCGTAGGTCCTGCTACTGAAGCCTTAGCCGGTGAAGGT
TTGATCGTAACGGCTGGTGGTATTGACACACACATCCACTTCATTTCACCCCAACAAATC
CCTACAGCTTTTCGAAGCGGTGTAACAACCATGATTGGTGGTGGAACCGGTCCTGCTGAT
GGCACTAATGCGACTACTATCACTCCAGGCAGAAGAAATTTAAAATGGATGCTCAGAGCG
GCTGAAGAATATTCTATGAATTTAGGTTTCTTGGCTAAAGGTAACGCTTCTAACGATGCG
AGCTTAGCCGATCAAATTGAAGCCGGTGCGATTGGCTTTAAAATTCACGAAGACTGGGGC
ACCACTCCTTCTGCAATCAATCATGCGTT;

or the following nucleotide sequence (V):

ATGAAACTCACCCCAAAAGAGTTAGATAAGTTGATGCTCCACTACGCTGGAGAATTGGCT
AAAAAACGCAAAGAAAAAGGCATTAAGCTTAACTATGTAGAAGCAGTAGCTTTGATTAGT
GCCCATATTATGGAAGAAGCGAGAGCTGGTAAAAAGACTGCGGCTGAATTGATGCAAGAA
GGGCGCACTCTTTTAAAACCAGATGATGTGATGGATGGCGTGGCAAGCATGATCCATGAA
GTGGGTATTGAAGCGATGTTTCCTGATGGGACTAAACTCGTAACCGTGCATACCCCTATT
GAGGCCAATGGTAAATTAGTTCCTGGTGAGTTGTTCTTAAAAAATGAAGACATCACTATC
AACGAAGGCAAAAAAGCCGTTAGCGTGAAAGTTAAAAATGTTGGCGACAGACCGGTTCAA
ATCGGCTCACACTTCCATTTCTTTGAAGTGAATAGATGCCTAGACTTTGACAGAGAAAAA
ACTTTCGGTAAACGCTTAGACATTGCGAGCGGGACAGCGGTAAGATTTGAGCCTGGCGAA
GAAAAATCCGTAGAATTGATTGACATTGGCGGTAACAGAAGAATCTTTGGATTTAACGCA
TTGGTTGATAGACAAGCAGACAACGAAAGCAAAAAAATTGCTTTACACAGAGCTAAAGAG
CGTGGTTTTCATGGCGCTAAAAGCGATGACAACTATGTAAAAACAATTAAGGAGTAA;

or the following nucleotide sequence (VII):

ATGAAAAAGATTAGCAGAAAAGAATATGTTTCTATGTATGGTCCTACTACAGGCGATAAA
GTGAGATTGGGCGATACAGACTTGATCGCTGAAGTAGAACATGACTACACCATTTATGGC
GAAGAGCTTAAATTCGGTGGCGGTAAAACCCTAAGAGAAGGCATGAGCCAATCTAACAAC
CCTAGCAAAGAAGAGTTGGATTTAATTATCACTAACGCTTTAATCGTGGATTACACCGGT
ATTTATAAAGCGGATATTGGTATTAAAGATGGCAAAATCGCTGGCATTGGTAAAGGCGGT
AACAAAGACATGCAAGATGGCGTTAAAAACAATCTTAGCGTAGGTCCTGCTACTGAAGCC
TTAGCCGGTGAAGGTTTGATCGTAACGGCTGGTGGTATTGACACACACATCCACTTCATT
TCACCCCAACAAATCCCTACAGCTTTTGCAAGCGGTGTAACAACCATGATTGGTGGTGGA
ACCGGTCCTGCTGATGGCACTAATGCGACTACTATCACTCCAGGCAGAAGAAATTTAAAA
TGGATGCTCAGAGCGGCTGAAGAATATTCTATGAATTTAGGTTTCTTGGCTAAAGGTAAC
GCTTCTAACGATGCGAGCTTAGCCGATCAAATTGAAGCCGGTGCGATTGGCTTTAAAATT
CACGAAGACTGGGGCACCACTCCTTCTGGAATCAATCATGCGTTAGATGTTGCGGACAAA

-continued

TACGATGTGCAAGTCGCTATCCACACAGACACTTTGAATGAAGCCGGTTGTGTAGAAGAC

ACTATGGCTGCTATTGCTGGACGCACTATGCACACTTTCCACACTGAAGGCGCTGGCGGC

GGACACGCTCCTGATATTATTAAAGTAGCCGGTGAACACAACATTCTTCCCGCTTCCACT

AACCCCACCATCCCTTTCACCGTGAATACAGAAGCAGAGCACATGGACATGCTTATGGTG

TGCCACCACTTGGATAAAAGCATTAAAGAAGATGTTCAGTTCGCTGATTCAAGGATCCGC

CCTCAAACCATTGCGGCTGAAGACACTTTGCATGACATGGGGATTTTCTCAATCACCAGT

TCTGACTCTCAAGCGATGGGCCGTGTGGGTGAAGTTATCACTAGAACTTGGCAAACAGCT

GACAAAAACAAGAAAGAATTTGGCCGCTTGAAAGAAGAAAAAGGCGATAACGACAACTTC

AGGATCAAACGCTACTTGTCTAAATACACCATTAACCCAGCGATCGCTCATGGGATTAGC

GAGTATGTAGGTTCAGTAGAAGTGGGCAAAGTGGCTGACTTGGTATTGTGGAGTCCAGCA

TTCTTTGGCGTGAAACCCAACATGATCATCAAAGGCGGATTCATTGCGTTAAGCCAAATG

GGCGATGCGAACGCTTCTATCCCTACCCCACAACCGGTTTATTACAGAGAAATGTTCGCT

CATCATGGTAAAGCTAAATACGATGCAAACATCACTTTTGTGTCTCAAGCGGCTTATGAC

AAAGGCATTAAAGAAGAATTAGGACTTGAAAGACAAGTGTTGCCGGTAAAAAATTGCAGA

AATATCACTAAAAAAGACATGCAATTCAACGACACTACTGCTCACATTGAAGTCAATCCT

GAAACTTACCATGTGTTCGTGGATGGCAAAGAAGTAACTTCTAAACCAGCCAATAAAGTG

AGCTTGGCGCAACTCTTTAGCATTTTCTAG or the nucleotide sequences complementary to the above-mentioned sequences (I), (II), (V) and (VII), respectively,
wherein said purified nucleotide sequence specifically hybridizes with a probe sequence from *C. pylori* and not with a probe sequence from *C. jejuni, C. fetus* or *C. coli.*

3. A purified nucleic acid probe that specifically hybridizes with a nucleotide sequence encoding the urease expressed by *Campylobacter pylori.*

4. The nucleic acid probe of claim 3, wherein said probe is detectably labeled.

5. The nucleic acid probe of claim 3, wherein the length of said probe is about 25 to 40 nucleotides.

6. A kit for detecting the presence of *Campylobacter pylori* in a sample, said kit comprising:
the nucleic acid probe of claim 3, and
a medium suitable for hybridizing said probe to a nucleotide sequence to be detected.

7. A method of detecting *Campylobacter pylori* in a sample, said method comprising:
contacting said sample with the nucleic acid probe of claim 3 under conditions sufficient to permit hybridization of said probe with a *Campylobacter pylori* nucleotide sequence, which encodes a protein having urease activity, and
detecting the formation of the resulting hybridization complex, whereby the presence or absence of *Campylobacter pylori* is detected.

8. An isolated nucleotide sequence, which according to the universal genetic code, encodes the following amino acid sequence (III):

9. An isolated nucleotide sequence corresponding, according to the universal genetic code, to the following amino acid sequence (IV):

KLLGVLGVYQKSKNALSSQAIVATNMSNLALKEYLXSQDLELKHCAIGDKFVSECMRLNK

ANFGGEQSGHIIFSDYAKTGDGLVCALQVSALVLESKL.

NMTTPFMAKSLNSVAVKPLREGMSQSNNPSKEELDLIITNALIVDYTGIYKADIGTKDGK

LAGIGKGGNKDMQDGVKNNLSVGPATEALAGEGLIVTAGGIDTHIHFISPQQIPTAFRSG

VTTMIGGGTGPADGTNATITTPGRRNLKWMLRAAEEYSMNLGFLAKGNASNDASLADQIE

AGAIGFKIHEDWGTTPSAINHA.

10. A nucleic acid probe that specifically hybridizes with a nucleotide sequence, said hybridization occurring under conditions of 68° C. and 6×SSC in Denhardt medium, wherein said nucleotide sequence is selected from the group consisting of (I):
AAGCTTTTAGGGGTGTTAGGGGTTTATCAAAAATCTAAAAACGCCCTTTCTTCTCAAGCA
ATTGTCGCTACAAACATGAGCAATTTAGCCCTTAAAGAATACTTAAAATCCCAAGATTTA
GAATTGAAGCATTGCGCGATTGGGGATAAGTTTGTGAGCGAATGCATGCGATTGAACAAA
GCCAATTTTGGAGGCGAGCAAAGCGGGCATATCATTTTTAGCGATTACGCTAAAACCGGC
GATGGCTTGGTGTGCGCTTTGCAAGTGAGCGCGTTAGTGTTAGAAAGTAAGCTT;

(II):
CCTAAAAGCGATGACAACTATGTAAAAACAATTAAGGAGTAAGAAATGAAAAAGATTAGC
AGAAAAGAATATGTTTCTATGTATGGTCCTACTACAGGCGATAAAGTGAGATTGGGCGAT
CAGACTTGATCGCTGAAGTAGAACATGACTACACCATTTATGGCGAAGAGCTTAAATTCG
GTGGCGGTAAAACCCCTAAGAGAAGGCATGAGCCAATCTAACAACCCTAGCAAAGAAGAG
TTGGATTTAATTATCACTAACGCTTTAATCGTGGATTACACCGGTATTTATAAAGCGGAT
ATTGGTATTAAAGATGGCAAAATCGCTGGCATTGGTAAAGGCGGTAACAAAGACATGCAA
GATGGCGTTAAAAACAATCTTAGCGTAGGTCCTGCTACTGAAGCCTTAGCCGGTGAAGGT
TTGATCGTAACGGCTGGTGGTATTGACACACACATCCACTTCATTTCACCCCAACAAATC
CCTACAGCTTTTCGAAGCGGTGTAACAACCATGATTGGTGGTGGAACCGGTCCTGCTGAT
GGCACTAATGCGACTACTATCACTCCAGGCAGAAGAAATTTAAAATGGATGCTCAGAGCG
GCTGAAGAATATTCTATGAATTTAGGTTTCTTGGCTAAAGGTAACGCTTCTAACGATGCG
AGCTTAGCCGATCAAATTGAAGCCGGTGCGATTGGCTTTAAAATTCACGAAGACTGGGGC
ACCACTCCTTCTGCAATCAATCATGCGTT;

(V):
ATGAAACTCACCCCAAAAGAGTTAGATAAGTTGATGCTCCACTACGCTGGAGAATTGGCT
AAAAAACGCAAAGAAAAAGGCATTAAGCTTAACTATGTAGAAGCAGTAGCTTTGATTAGT
GCCCATATTATGGAAGAAGCGAGAGCTGGTAAAAAGACTGCGGCTGAATTGATGCAAGAA
GGGCGCACTCTTTTAAAACCAGATGATGTGATGGATGGCGTGGCAAGCATGATCCATGAA
GTGGGTATTGAAGCGATGTTTCCTGATGGGACTAAACTCGTAACCGTGCATACCCCTATT
GAGGCCAATGGTAAATTAGTTCCTGGTGAGTTGTTCTTAAAAAATGAAGACATCACTATC
AACGAAGGCAAAAAAGCCGTTAGCGTGAAAGTTAAAAATGTTGGCGACAGACCGGTTCAA
ATCGGCTCACACTTCCATTTCTTTGAAGTGAATAGATGCCTAGACTTTGACAGAGAAAAA
ACTTTCGGTAAACGCTTAGACATTGCGAGCGGGACAGCGGTAAGATTTGAGCCTGGCGAA
GAAAAATCCGTAGAATTGATTGACATTGGCGGTAACAGAAGAATCTTTGGATTTAACGCA
TTGGTTGATAGACAAGCAGACAACGAAAGCAAAAAAATTGCTTTACACAGAGCTAAAGAG
CGTGGTTTTCATGGCGCTAAAAGCGATGACAACTATGTAAAAACAATTAAGGAGTAA;

and (VII):
ATGAAAAAGATTAGCAGAAAAGAATATGTTTCTATGTATGGTCCTACTACAGGCGATAAA
GTGAGATTGGGCGATACAGACTTGATCGCTGAAGTAGAACATGACTACACCATTTATGGC
GAAGAGCTTAAATTCGGTGGCGGTAAAACCCTAAGAGAAGGCATGAGCCAATCTAACAAC
CCTAGCAAAGAAGAGTTGGATTTAATTATCACTAACGCTTTAATCGTGGATTACACCGGT
ATTTATAAAGCGGATATTGGTATTAAAGATGGCAAAATCGCTGGCATTGGTAAAGGCGGT
AACAAAGACATGCAAGATGGCGTTAAAAACAATCTTAGCGTAGGTCCTGCTACTGAAGCC
TTAGCCGGTGAAGGTTTGATCGTAACGGCTGGTGGTATTGACACACACATCCACTTCATT
TCACCCCAACAAATCCCTACAGCTTTTGCAAGCGGTGTAACAACCATGATTGGTGGTGGA
ACCGGTCCTGCTGATGGCACTAATGCGACTACTATCACTCCAGGCAGAAGAAATTTAAAA
TGGATGCTCAGAGCGGCTGAAGAATATTCTATGAATTTAGGTTTCTTGGCTAAAGGTAAC
GCTTCTAACGATGCGAGCTTAGCCGATCAAATTGAAGCCGGTGCGATTGGCTTTAAAATT
CACGAAGACTGGGGCACCACTCCTTCTGGAATCAATCATGCGTTAGATGTTGCGGACAAA
TACGATGTGCAAGTCGCTATCCACACAGACACTTTGAATGAAGCCGGTTGTGTAGAAGAC
ACTATGGCTGCTATTGCTGGACGCACTATGCACACTTTCCACACTGAAGGCGCTGGCGGC
GGACACGCTCCTGATATTATTAAAGTAGCCGGTGAACACAACATTCTTCCCGCTTCCACT
AACCCCACCATCCCTTTCACCGTGAATACAGAAGCAGAGCACATGGACATGCTTATGGTG
TGCCACCACTTGGATAAAAGCATTAAAGAAGATGTTCAGTTCGCTGATTCAAGGATCCGC
CCTCAAACCATTGCGGCTGAAGACACTTTGCATGACATGGGGATTTTCTCAATCACCAGT
TCTGACTCTCAAGCGATGGGCCGTGTGGGTGAAGTTATCACTAGAACTTGGCAAACAGCT
GACAAAACAAGAAAAGAATTTGGCCGCTTGAAAGAAGAAAAAAGGCGATAACGACAACTTC
AGGATCAAACGCTACTTGTCTAAATACACCATTAACCCAGCGATCGCTCATGGGATTAGC
GAGTATGTAGGTTCAGTAGAAGTGGGCAAAGTGGCTGACTTGGTATTGTGGAGTCCAGCA
TTCTTTGGCGTGAAACCCAACATGATCATCAAAGGCGGATTCATTGCGTTAAGCCAAATG
GGCGATGCGAACGCTTCTATCCCTACCCCACAACCGGTTTATTACAGAGAAATGTTCGCT
CATCATGCTAAAGCTAAATACGATGCAAACATCACTTTTGTGTCTCAAGCGGCTTATGAC
AAAGGCATTAAAGAAGAATTAGGACTTGAAAGACAAGTGTTGCCGGTAAAAAATTGCAGA -continued AATATCACTAAAAAAGACATGCAATTCAACGACACTACTGCTCACATTGAAGTCAATCCT
GAAACTTACCATGTGTTCGTGGATGGCAAAGAAGTAACTTCTAAACCAGCCAATAAAGTG
AGCTTGGCGCAACTCTTTAGCATTTTCTAG.

11. The nucleic acid probe of claim 10, wherein said probe is detectably labeled.

12. The nucleic acid probe of claim 10, wherein the length of said probe is about 25 to 40 nucleotides.

13. A method of detecting Campylobacter pylori in a sample, said method comprising the steps of:

contacting said sample with the nucleic acid probe of claim 10 under conditions sufficient to permit hybridization of said probe with a *Campylobacter pylori* nucleotide sequence that encodes a protein having urease activity, and detecting the formation of the resulting hybridization complex, whereby the presence of *Campylobacter pylori* is detected.

14. A method of detecting *Campylobacter pylori* as claimed in claim 13, wherein contacting said sample with said nucleic acid probe occurs at about 68° C. and in 6×SSC in Denhardt medium.

15. A purified nucleotide sequence which hybridizes under stringent conditions of 68° C. and 6×SSC in Denhart medium with the genes coding for *Campylobacter pylori* urease.

* * * * *

UNITED STATES PATENT AND TRADEMARK OFFICE
CERTIFICATE OF CORRECTION

PATENT NO. : 5,811,237

DATED : September 22, 1998

INVENTOR(S) : Agnes LABIGNE et al.

It is certified that error appears in the above-indentified patent and that said Letters Patent is hereby corrected as shown below:

On the title page, item

[*] Notice: line 3, delete "5,610,707" and insert therefor --5,695,931--.

Signed and Sealed this

Sixteenth Day of February, 1999

Attest:

Attesting Officer

Acting Commissioner of Patents and Trademarks